United States Patent
Iwayama et al.

(10) Patent No.: US 6,320,087 B2
(45) Date of Patent: *Nov. 20, 2001

(54) ADSORBENT FOR SEPARATING HALOGENATED AROMATIC COMPOUNDS AND SEPARATION METHOD

(75) Inventors: Kazuyoshi Iwayama; Shinobu Yamakawa; Masashi Kato; Hirohito Okino, all of Aichi (JP)

(73) Assignee: Toray Industries, Inc. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/287,044

(22) Filed: Apr. 6, 1999

(30) Foreign Application Priority Data

Apr. 9, 1998 (JP) .................................. 10-097957

(51) Int. Cl.⁷ ...................................... C07C 17/38
(52) U.S. Cl. ............................. 570/179; 570/262
(58) Field of Search ...................... 570/179, 262; 502/79

(56) References Cited

U.S. PATENT DOCUMENTS

| 4,254,062 | 3/1981 | Wambach et al. . |
| 4,698,453 | 10/1987 | Miwa et al. . |

FOREIGN PATENT DOCUMENTS

| 0322869 | 7/1989 | (EP) . |
| 62-292736 | 5/1988 | (JP) . |
| 4-013639 | 4/1992 | (JP) . |
| 9-188638 | 11/1997 | (JP) . |
| 2292736 | * 12/1987 | (JP) ................................ 570/179 |

* cited by examiner

*Primary Examiner*—Alan Siegel
(74) *Attorney, Agent, or Firm*—Schnader Harrison Segal & Lewis LLP (57) ABSTRACT

An adsorbing and separating agent for halogenated aromatic compounds and an adsorbing and separating method for the compounds, using an adsorbent which has a porosity of from 0.20 cc/cc to 0.37 cc/cc, a packing density of from 0.50 g/ml to 0.70 g/ml, and a grain size of from 0.1 mm to 1.0 mm.

7 Claims, 6 Drawing Sheets

SCHEMATIC VIEW SHOWING A DEVICE FOR MEASURING THE PACKING DENSITY OF AN ADSORBENT

FIG.1

SCHEMATIC VIEW SHOWING SIMULATED-
MOVING BED

FIG.2

FIG. 3 PORE VOLUME DISTRIBUTION OF ADSORBENTS

*FIG. 4* PERFORMANCE OF THE ADSORBENTS FOR A CEB ISOMER MIXTURE

FIG. 5  PERFORMANCE OF THE ADSORBENTS FOR A DCB ISOMER MIXTURE

*FIG. 6* THE RELATION BETWEEN THE AMOUNT OF THE ISOMER MIXTURE PROCESSED AND THE ADSORPTIVE SELECTIVITY

ADSORBENT FOR SEPARATING HALOGENATED AROMATIC COMPOUNDS AND SEPARATION METHOD

TECHNICAL FIELD

The present invention relates to an adsorbent for separating halogenated aromatic hydrocarbons and to a method of using it for separating an isomer from a mixture of halogenated aromatic isomers.

BACKGROUND OF THE INVENTION

Halogenated aromatic compounds are of much industrial importance as intermediates for medicines, agricultural chemicals, etc. At present, these intermediates are required to have much higher purity than heretofore. Except for monohalogenated benzenes, aromatic compounds with two or more substituents each have different isomers. For separating the mixture of those isomers into individual isomers through ordinary industrial distillation, an ultra-precision distillation device is needed, since the difference in boiling points between the isomers is small. However, at present, it is still extremely difficult to obtain high-purity products of a single isomer on an industrial scale. In addition, some types of halogenated aromatic compounds could not be separated into individual isomers through distillation. Recently, for separating a mixture of isomers that have heretofore been difficult or impossible to separate into individual ones, methods using adsorption separation have been developed. For example, JP-A 57-91933 and 58-131923 disclose a method of separating a single isomer from a mixture of chlorotoluene isomers through adsorption. Japanese Patent Application No. 9-335225 discloses a method of separating a single isomer from a mixture of chloroethylbenzene isomers through adsorption. JP-A 52-62229, 53-105434, 58-131924, 58-150524, 62-175433 and 4-330025 disclose a method of separating a single isomer from a mixture of dichlorobenzene isomers. JP-A 59-199642, 60-42340, 5-70383, 58-137795 and 3-20232 disclose a method of separating a mixture of dichlorotoluene isomers. JP-B 4-46933 discloses a process comprising removing HCl and water, which are formed in isomerization of a halogenated benzene derivative, through distillation, followed by separating a specific single isomer from the mixture of the resulting isomers by the use of an adsorbing and separating zeolite.

SUMMARY OF THE INVENTION

Increasing the purity of the single isomer to be separated in those adsorption separation methods, and increasing the separation efficiency therein, is extremely important to the industrial effect. However, the methods mentioned above are not satisfactory with respect to the purity of the single isomer separated.

In using an adsorbing and separating agent that comprises zeolite for separating a single isomer from a mixture of halogenated aromatic compound isomers, the capabilities of the adsorbing and separating agent being used are lowered with the lapse of time. In the method, therefore, the adsorbing and separating agent being used must be exchanged for a fresh one or must be regenerated through firing or the like. Therefore, prolonging the life of the agent and prolonging the regeneration cycle for the agent is extremely advantageous to the industrial effect. However, the conventional techniques are unsatisfactory with respect to the prolongation of the life of the agent and to the prolongation of the regeneration cycle.

The invention is directed to solve the problems noted above, and to provide an efficient method for separating halogenated aromatic compound isomers.

In order to solve these problems, we, the present inventors have assiduously studied the capabilities of adsorbents for improving them. Adsorbents consist essentially of zeolite. Zeolite includes natural zeolite and synthetic zeolite, of which synthetic zeolite is especially preferably used. Synthetic zeolite is generally in the form of powder. For using zeolite as an industrial adsorbent, it must be shaped. Specifically, zeolite adsorbents are generally in the form of shaped articles. Having noticed the shaped articles of zeolite as adsorbents, we have investigated the factors that may govern the capabilities of zeolite to adsorb and separate halogenated aromatic compounds. As a result, we have found that the packing density of the adsorbent, the porosity of the adsorbent and the grain size of the adsorbent are important factors.

The packing density of an adsorbent depends on the porosity thereof, the shape thereof, etc. An adsorbent having a higher packing density is preferred, since its amount filled in a unit volume increases and since a larger amount of the adsorbent could be filled in an adsorbent tower. However, for an adsorbent having too high packing density, it has been found that its adsorbing and separating capabilities are lowered.

The porosity of an adsorbent is caused by the macro pores existing in the adsorbent. An adsorbent having too high porosity is unfavorable, since its packing density is lowered. Contrary to this, for an adsorbent having too low porosity, the volume of macro pores existing therein is too small. As a result, it has been found that, when a halogenated aromatic compound is applied to the adsorbent of zeolite of that type, it is prevented from being diffused in the adsorbent grains before it reaches the pores through which the compound is adsorbed by the adsorbent, zeolite, and therefore the adsorbing and separating capabilities of the adsorbent are poor.

On the other hand, it has been found that a shaped adsorbent comprising smaller grains could have higher adsorbing and separating capabilities. It is believed that, in zeolite adsorbent grains having a small grain size, the pathway through which a halogenated aromatic compound to be adsorbed by the grains are diffused into the pores of the zeolite grains will be shortened, whereby the compound could be rapidly adsorbed by the grains. It is considered that the diffusion of halogenated aromatic compounds into adsorbent grains will be much influenced by the grain size of the grains, as compared with that of halogen-free aromatic hydrocarbons. This will be probably related to the fact that halogens, for example, chlorine and bromine have a large ionic radius or a large atomic weight. However, adsorbent grains having a too small grain size are unfavorable, since they will cause increase in pressure loss.

We, the present inventors have studied production methods for aromatic compounds, and, as a result, have found that using a halogenated aromatic compound having a dissolved oxygen content of at most 15 ppm by weight prevents the deterioration of an adsorbing and separating agent and prolongs the life of the agent, and that a halogenated aromatic compound can be efficiently separated.

Specifically, the invention provides an adsorbent for separating a halogenated aromatic compound, which adsorbent is characterized by having a packing density of from 0.50 g/ml to 0.70 g/ml, a porosity of from 0.2 to 0.37 cc/cc, and a grain size of from 0.1 mm to 1.0 mm; a method of using the adsorbent for separating at least one halogenated aromatic compound isomer from a mixture of halogenated aromatic compound isomers; and a method for separating at least one halogenated aromatic compound isomer, which comprises contacting a mixture of halogenated aromatic compound isomers having a dissolved oxygen content of at most 15 ppm by weight with an adsorbent for separating halogenated aromatic compounds.

DETAILED DESCRIPTION OF THE PREFERRED EMBODIMENTS

The essential component in the adsorbent of the invention is synthetic zeolite. Examples of the zeolite usable herein include faujasite-type zeolite, MFI-type zeolite and beta-type zeolite. Most preferred is faujasite-type zeolite. Faujasite-type zeolite is a crystalline aluminosilicate represented by the following general formula in terms of the molar ratio of the oxides constituting it:

$$M_{2/n}O \cdot Al_2O_3 \cdot xSiO_2 \cdot yH_2O$$

wherein M represents a metal ion or a hydrogen ion; n represents the valence of the metal ion or the hydrogen ion; x represents the molar ratio of silica/alumina. One with x of smaller than 3 is referred to as X-type zeolite, and one with an x value of 3 or more is referred to as Y-type zeolite. In the formula, y varies depending on the degree of hydration.

Synthetic zeolite is generally obtained in the form of powder. For shaping the powder, for example, any method of kneading, rolling or compression is employed. In the invention, a kneading method is preferred. In shaping the powder, a binder is often used for increasing the mechanical strength and the packing density of the shaped articles. As the binder, preferred are alumina, bentonite, kaolin, etc. Depending on the intended mechanical strength and packing density of the shaped articles, the amount of the binder to be used may fall between 5 and 40% by weight, preferably between 10 and 20% by weight. In view of the zeolite content of the shaped articles, it is desirable that the amount of the binder is smaller. However, the uppermost limit and the lowermost limit of the amount of the binder to be used shall be determined, depending on the type of the binder and the intended mechanical strength of the shaped articles. The amount of the binder also depends on the crystal structure and the crystal morphology of the zeolite.

For shaping zeolite in a kneading method, zeolite powder, binder, water and optionally surfactant the to improve the shapability are well kneaded. The surfactant optionally used herein includes, for example, anionic surfactants (e.g., triethanolamine oleate, sodium oleate), cationic surfactants (e.g., N-cetyl-N-ethyl morpholinium Et sulfate as a trade name "Atlas G-251"), nonionic surfactants (e.g., oleic acid, sorbitan trioleate as a trade name "Span 85", sorbitan monooleate as a trade name "Span 80", sorbitan monolaurate as a trade name "Span 20", polyoxyethylene sorbitan monostearate as a trade name "Tween 60", polyoxyethylene sorbitan monooleate as a trade name "Tween 80", polyoxyethylene sorbitan monolaurate as a trade name "Tween 20").

The kneaded mixture is extruded through an extruder, for which the screen mesh is suitably selected to control the grain size of the intended adsorbent grains. The extruded adsorbent grains are then processed in a rounding machine (Marumerizer), in which their length is controlled, or they are rounded. Through the rounding operation, the packing density of the adsorbent grains and the porosity could be controlled in some degree.

The shaped adsorbent is then dried for removing water therefrom. The drying temperature may generally fall between 50 and 200° C. After having been dried, the adsorbent is then calcined to thereby have increased mechanical strength. The calcination temperature generally falls between 350 and 700° C.

The adsorbent thus having been calcined to have an increased mechanical strength is thereafter optionally subjected to cation exchange treatment, depending on the type of the halogenated aromatic compound to be treated with it. For the ion exchange treatment, employable is any cation generally employed in the art.

The packing density of the adsorbent may vary in some degree, depending on the measuring method used. The packing density of the adsorbent of the invention is measured according to the method mentioned below.

(1) The empty weight of a measuring container is measured, and this is referred to as (A). The container is prepared by cutting a 250-ml messcylinder having an outer diameter of 40 mmφ, at a height of 200 mmH from its bottom, and its volume, V, is previously determined with water.

Figure 1:
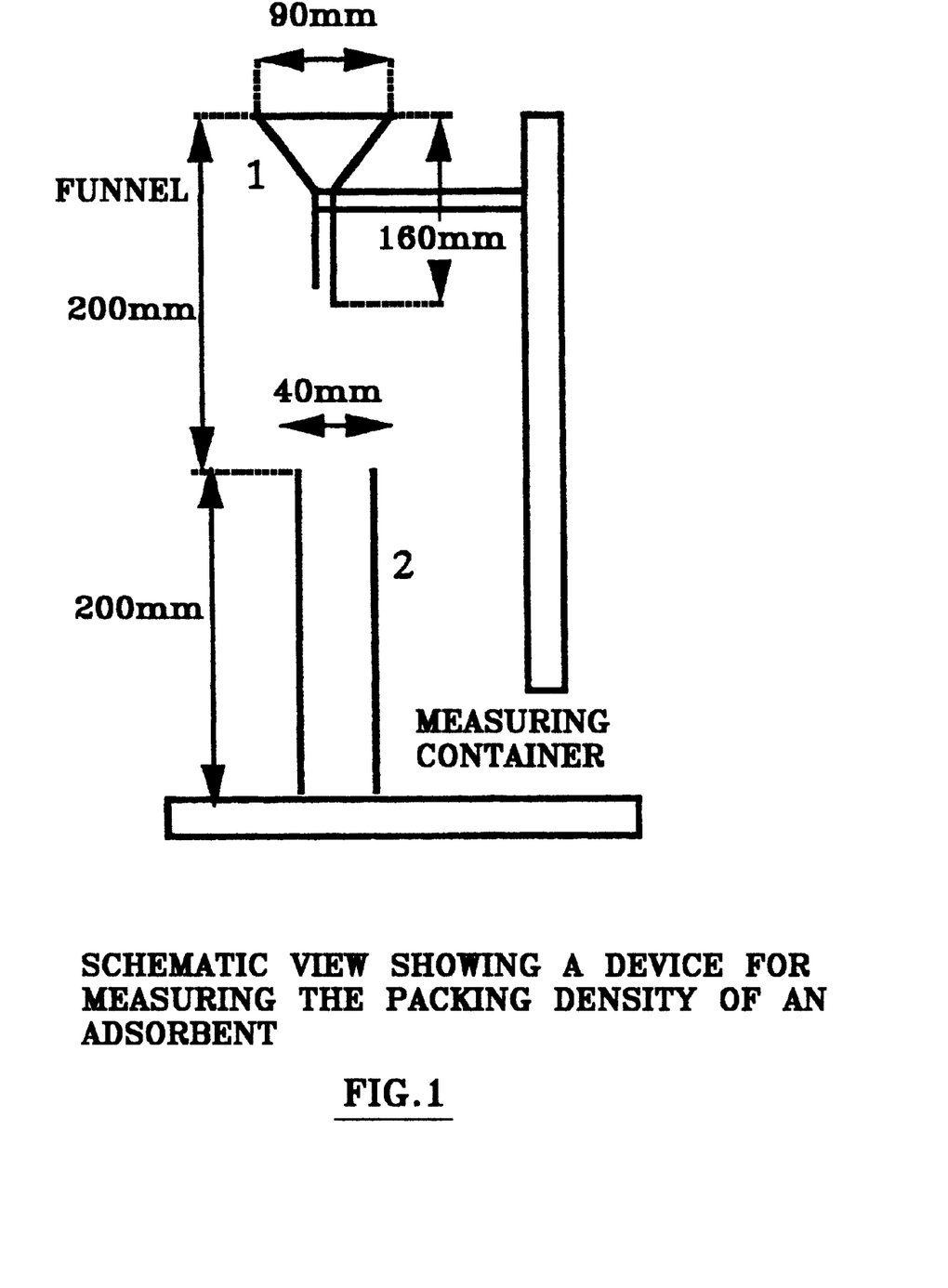
FIG. 1 is a schematic view showing a device for measuring the packing density of an adsorbent.

(2) The measuring equipment is set as in FIG. 1.

(3) About 300 ml of a calcined adsorbent (sample) is taken in a glass beaker.

(4) The distance between the top of the measuring container and the top of the funnel is settled to be 200 mm, and the sample in the glass beaker is fed into the funnel, while being dropped into the container through the funnel to heap up.

(Note: The sample is dropped into the center of the container, messcylinder, and the measuring equipment must not be moved during the measurement.)

(5) After the sample has been dropped into the container, its heaped part is gently scraped off with a scale to be flat.

(6) The weight of the container with the sample therein is measured, and this is referred to as (B).

(Note: As the sample is highly hygroscopic, the operation of (1) to (6) must be effected rapidly.)

(7) The measurement is repeated twice, and the average value is obtained.

(8) A 30-ml ceramic crucible that has been previously calcined at 500° C. for 1 hour is weighed. About 2 g of the same sample as above is accurately weighed and put into the crucible, which is then calcined at 500° C. for 1 hour. This is cooled in a desiccator for about 15 minutes. After having reached room temperature, this is weighed. From the thus-weighed dry weight of the sample, calculated is the water content (% by weight) of the non-dried sample.

(9) The packing density (ABD) of the sample is calculated according to the following equation:

$$ABD \text{ (g/ml)} = \frac{B-A}{V} \times \left(1 - \frac{100 - \text{water content}}{100}\right)$$

wherein;

A indicates the weight of the empty container (g),

B indicates the weight of the sample (adsorbent)+A (g), and

V indicates the volume of the measuring container (ml).

An adsorbent having a higher packing density is preferred, since the amount capable of being filled in its unit volume increases. However, an adsorbent having a too high packing density is unfavorable, since its adsorbing and separating capabilities for halogenated aromatic compounds are poor.

The porosity of an adsorbent can be measured with ease, according to a method of mercury penetration, for which a porosimeter is used. Concretely, the porosity of the adsorbent of the invention is measured in the manner mentioned below.

The adsorbent to be measured is put in an electric furnace, calcined therein at 500° C. for 2 hours, and then cooled in a desiccator to reach room temperature. This is put in a sample cell, and is thereafter filled with mercury in vacuum. Then, this is set in a porosimeter device. Pressure is applied thereto, whereupon the volume of mercury penetrated into the pores of the adsorbent grains is electrically detected. Thus is obtained the relationship between the pressure Pm[psi] and the pore volume [cc]. This measurement is repeated under different pressures. The pressure Pm is converted into the pore radius, r, according to the following equation (1):

$$r = -2\gamma \cos \theta / P \quad (1)$$

wherein;

r indicates the radius of pores into which mercury penetrates under a pressure P, [Å], P indicates a pressure, P=Pm[psi]×6.89476×10³[N/m.m], γ indicates the surface tension of mercury, 0.484[N/m], and θ indicates the contact angle of mercury to the sample (adsorbent), 141.3[°].

The volume of the adsorbent grains is obtained as follows: The adsorbent grains to be measured are put into a sample cell. The volume as expelled by the adsorbent grains to which is added mercury in vacuum, and the pore volume of the grains having a pore diameter of up to 3 µm to which is added mercury under pressure are summed up, and the total is the volume of the adsorbent grains. The pore volume is the accumulated volume of mercury as penetrated into the grains having a pore diameter of from 3 µm to 10 nm. Accordingly, the porosity (cc/cc) of the adsorbent grains is defined as follows:

$$\text{Porosity (cc/cc)} = \frac{(\text{pore volume (cc)})}{(\text{adsorbent grain volume (cc)})} \quad (2)$$

Adsorbent grains having a larger porosity are preferred, since a halogenated aromatic compound could more easily diffuse inside the grains. However, too large grains are unfavorable, since the packing density of the adsorbent is lowered. Preferably, the porosity of the adsorbent grains falls between 0.20 and 0.37 cc/cc, more preferably between 0.25 and 0.35 cc/cc.

The grain size of the adsorbent grains can be easily measured with a scale or a scale equipped with a magnifying glass. At least any 10 adsorbent grains are measured for their grain size, and the data are averaged. The resulting mean value is the grain size of the grains. In the invention, the grain size of the adsorbent grains preferably falls between 0.1 and 1.0 mm, more preferably between 0.2 and 0.8 mm. Adsorbent grains having a smaller grain size are preferred, since the pathway in each grain through which the adsorbed molecules diffuse in the grains is shorter. However, too small grains are unfavorable, since they cause the increase in pressure loss, and since their industrial production is not economical.

The halogen to be in the halogenated aromatic compounds to which the invention is directed includes fluorine, chlorine, bromine and iodine. Of those, favorable to the invention are chlorine and bromine, and more favorable is chlorine. It is also desirable that the halogenated aromatic compounds have at least one alkyl group. The alkyl group preferably has from 1 to 4 carbon atoms, and more preferred are methyl group, ethyl group and propyl group.

Specific examples of the halogenated aromatic compounds include fluorotoluene, chlorotoluene, bromotoluene, dichlorobenzene, dibromobenzene, fluorochlorobenzene, chlorobromobenzene, trichlorobenzene, dichlorofluorobenzene, dichlorobromobenzene, dibromochlorobenzene, dichlorotoluene, dibromotoluene, chloroxylene, bromoxylene, chloroethylbenzene, bromoethylbenzene, chlorocumene, chloropropylbenzene, bromocumene, bromopropylbenzene, chlorobutylbenzene, bromobutylbenzene, etc.

In the invention, when the dissolved oxygen content of the halogenated aromatic compound to be processed is not higher than 15 ppm by weight, the adsorbent used for the compound can be prevented from deterioration. Smaller dissolved oxygen content is better. Preferably, the dissolved oxygen content is at most 5 ppm by weight, more preferably at most 1 ppm by weight.

The dissolved oxygen content of the aromatic compound can be measured with a Beckman dissolved oxygen meter, a polarographic dissolved oxygen meter or the like.

To reduce the dissolved oxygen content of the aromatic compound to be at most 15 ppm by weight, for example, employable is any treatment of radiation, degassing, distillation, nitrogen sealing or the like.

In the invention, the radiation treatment is to contact a liquid of a dissolved oxygen-containing aromatic compound with an inert gas such as $N_2$ or the like, thereby removing the dissolved oxygen from the aromatic compound. For the radiation, for example, $N_2$ may be directly bubbled into a liquid of an aromatic compound as put in a tank, or, alternatively, $N_2$ may be contacted with a liquid of an aromatic compound in a countercurrent flow in a plate column or a packed column. The pressure for the operation may be normal pressure, elevated pressure or reduced pressure. Regarding the temperature for the operation, the operation is generally effected at a temperature at which the aromatic compound to be processed is in a liquid phase.

The degassing treatment includes, for example, a method of reducing the pressure in a tank as filled with a dissolved oxygen-containing aromatic compound, by the use a vacuum pump or the like; and a method of reducing the pressure in a plate column or a packed column as filled with a liquid of a dissolved oxygen-having aromatic compound to thereby remove the dissolved oxygen from the compound.

The pressure for the operation may be any of vacuum to normal pressure, but a lower pressure is preferred. The operation is generally effected at a temperature at which the aromatic compound to be processed can be in a liquid phase.

The distillation treatment may be effected in any ordinary manner. For this, the distillation tower may be a plate column, a packed column or the like, and the pressure may be of normal pressure, elevated pressure or reduced pressure.

The nitrogen sealing treatment serves to put a dissolved oxygen-containing aromatic compound into a nitrogen-sealed container, for example, a tank, before the compound is subjected to isomerization or adsorbing separation, so that the dissolved oxygen is removed from the compound through vapor-liquid equilibration.

If a halogenated aromatic compound to be subjected to adsorbing separation contains dissolved oxygen, the dissolved oxygen in the compound will form an oxygen-containing compound. Since the resulting oxygen-containing compound has strong polarity, and is therefore strongly adsorbed by the adsorbing and separating agent, whereby the adsorbing and separating capabilities of the agent are lowered. Therefore, reducing the dissolved oxygen content of the halogenated aromatic compound is effective for preventing the deterioration of the adsorbing and separating agent, and it is believed that the regeneration cycle for the agent may thereby be prolonged.

The technique of adsorbing and separating a single isomer from a mixture of halogenated aromatic compound isomers according to the invention may be attained in so-called partitioning chromatography, in partitioning adsorption using a simulated-moving bed line comprising a series of partitioning chromatography columns. In the simulated-moving bed line, the most easily adsorbable substance is collected in the extract flow, while the most difficulty adsorbable substance is collected in the raffinate flow.

The continuous adsorbing and separating technique using the simulated-moving bed line basically comprises adsorption, concentration, desorption and desorbent recovery, which are continuously repeated in that order. One example of a method of adsorbing and separating a mixture of chloroethylbenzene (hereinafter referred to as "CEB") isomers is mentioned below, in which m-CEB is adsorbed by the adsorbent used.

(1) Adsorption

A mixture of CEB isomers is contacted with an adsorbent, and a strongly adsorbable component, m-CEB is selectively adsorbed by the adsorbent, while the other weakly adsorbable components, o- and p-CEBs are recovered along with the desorbent in the form of a raffinate flow that will be mentioned below.

(2) Concentration

The adsorbent that has adsorbed the most strongly adsorbable component, m-CEB is then contacted with a part of the extract that will be mentioned below, and the weakly adsorbable components remaining on the adsorbent are removed, whereby the strongly adsorbable component is concentrated.

(3) Desorption

The adsorbent thus having the concentrated, most strongly adsorbable component, m-CEB is contacted with a desorbent, whereby the strongly adsorbable component is removed from the adsorbent, and recovered along with the desorbent in the form of an extract flow.

(4) Desorbent Recovery

The adsorbent thus having adsorbed substantially only the desorbent is contacted with a part of the raffinate flow, and a part of the desorbent having been adsorbed by the adsorbent is recovered in the form of a desorbent recovery flow.

Figure 2:
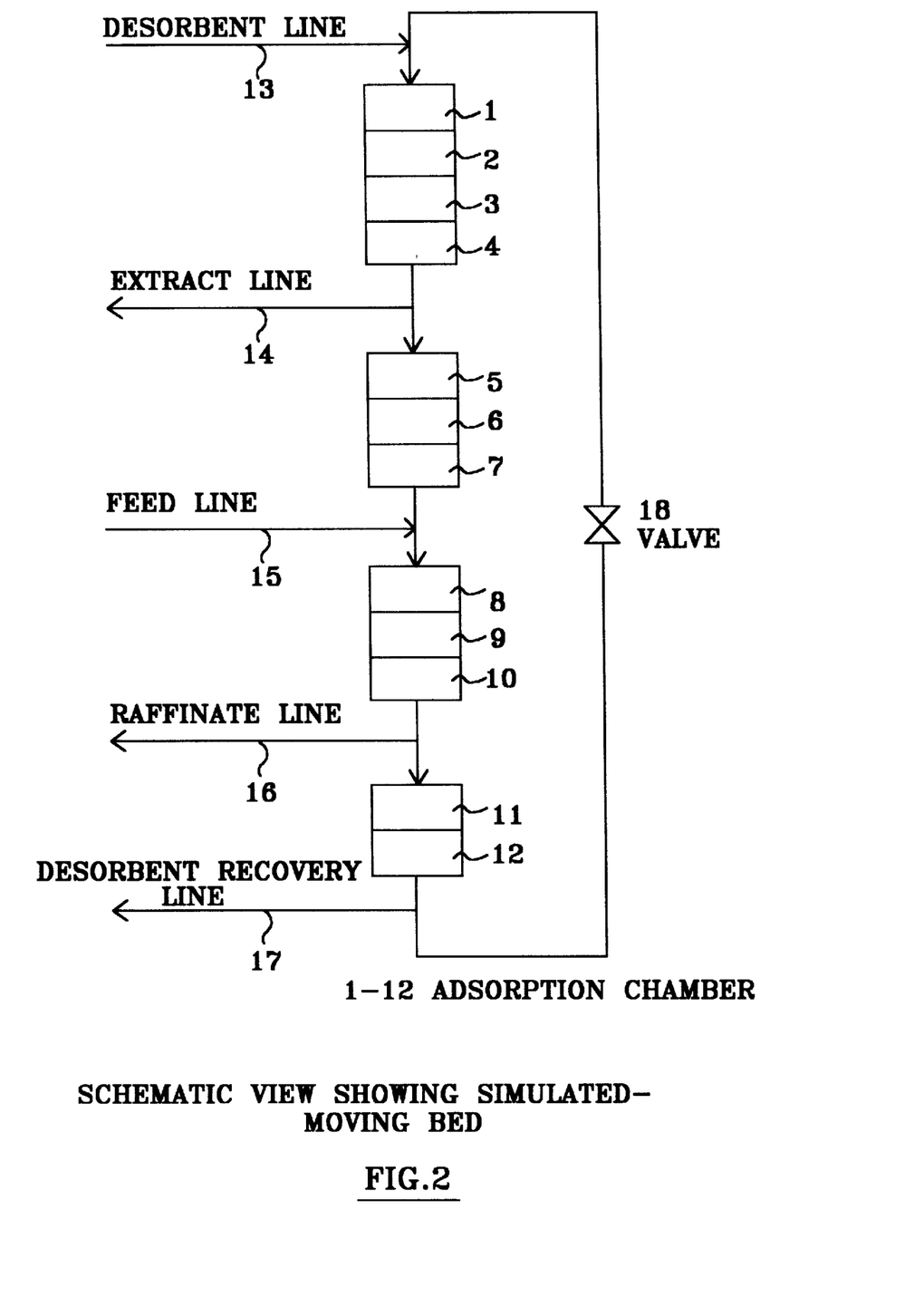
FIG. 2 is a schematic view showing the adsorption and separation process of one embodiment of the invention in a simulated-moving bed line.

FIG. 2 shows a schematic view showing the adsorption and separation process according to the simulated-moving bed line mentioned above. As in FIG. 2, adsorption chambers 1 to 12 all filled with an adsorbent are continuously connected with each other, through which the isomer mixture to be separated is circulated.

The adsorbing and separating operation for a halogenated aromatic compound is preferably effected in a liquid phase. A higher operation temperature is more preferred for higher diffusion rate of the compound being processed. Contrary to this, however, a lower operation temperature is more preferred for better adsorptive selectivity of the adsorbent used. Because of the contradictory temperature-dependent factors, the operation temperature will be preferably between 50 and 200° C.

EXAMPLES

Example 1

1.2 kg (dry weight) of Na-X zeolite powder (from Toso) having a molar ratio $SiO_2/Al_2O_3$ of 2.5, 0.96 kg of alumina sol (from Nissan Chemical, having an $Al_2O_3$ content of 10% by weight) and alumina gel (from Shokubai Kasei, having an $Al_2O_3$ content of 75% by weight) were mixed in a kneader (from Fuji Pawdal, Model KDHJ-10), and kneaded with a suitable amount of water added thereto, for about 1 hour. The resulting paste was extruded out through an extruder (from Fuji Pawdal, Model EXDS-60) equipped with a 0.3 mm-mesh screen, into pellets.

In order to round them and to increase their packing density, the resulting pellets were processed in a rounding machine (Marumerizer, Model QJ-230 from Fuji Pawdal), at a revolution of 850 rpm for 3 minutes.

Next, these were dried overnight at about 120° C. After having been dried, these were classified through a 80-mesh sieve to remove fine grains and through a 48-mesh sieve to remove coarse grains. The thus-classified grains were then calcined at 500° C. for 2 hours.

Figure 3:
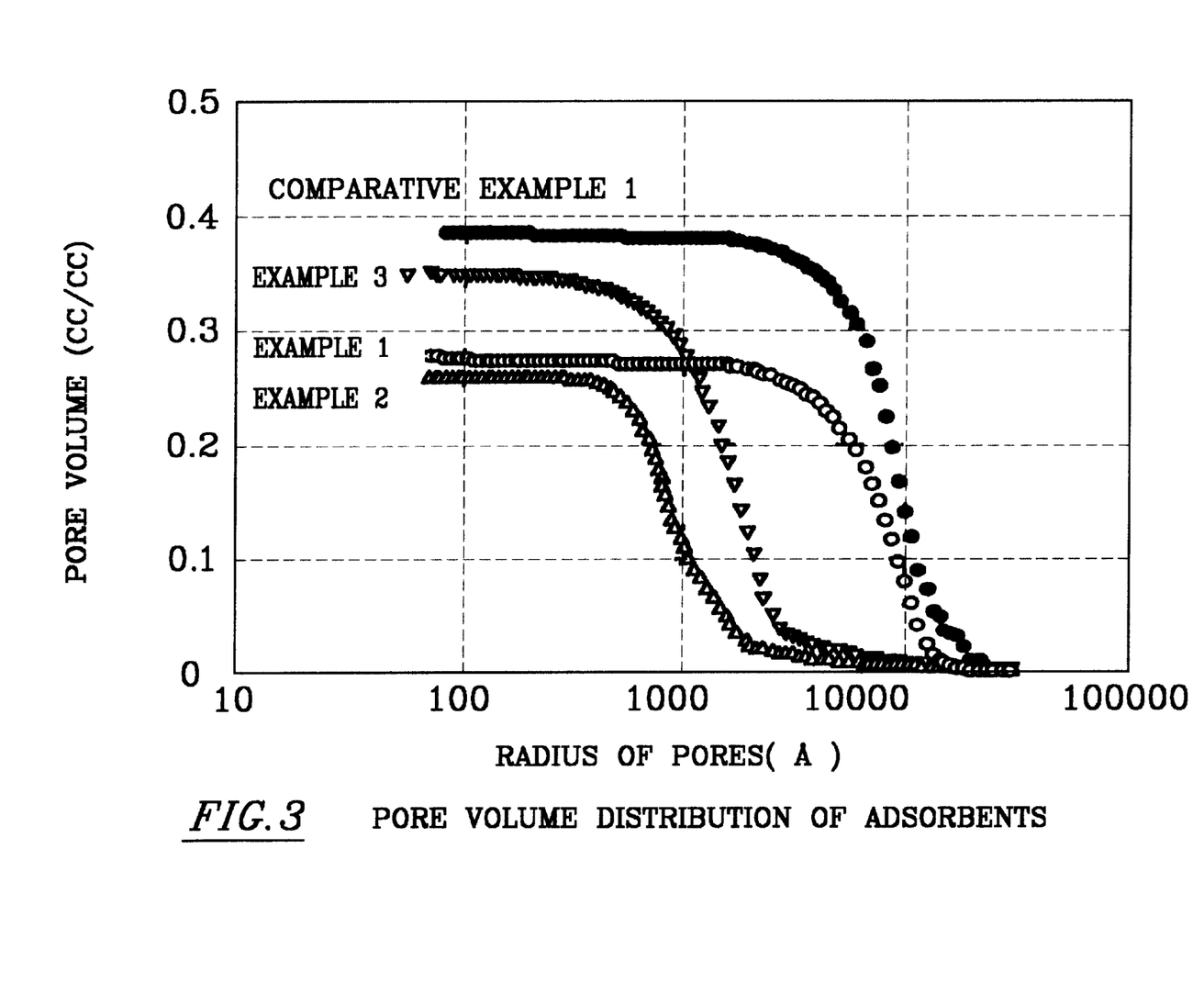
FIG. 3 is a graph showing the pore volume distribution of the adsorbents in Example 1 and Example 2.

The diameter of the adsorbent grains was measured with a scale equipped with a magnifying glass, and it was 0.3 mm. The length of the grains varied from about 0.3 mm to about 0.6 mm. The packing density of the adsorbent was 0.54 g/ml. The pore volume of the adsorbent grains was measured, and the data are shown in FIG. 3. The adsorbent had a porosity of 0.27 cc/cc.

Figure 4:
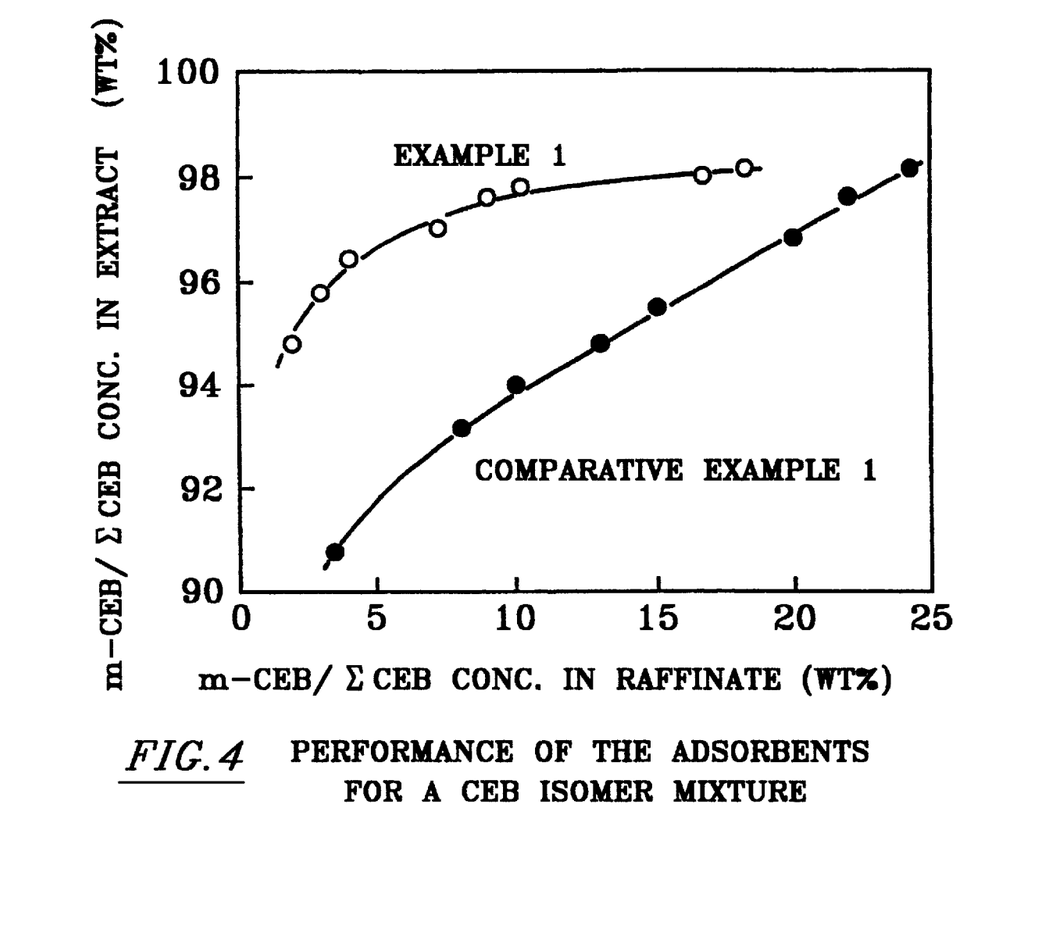
FIG. 4 is a graph showing the adsorbing and separating capabilities of the adsorbents for a CEB isomer mixture in Example 1 and Comparative Example 1.

The adsorbent was filled into 12 columns each having a size of 4.6 mmφ×1 m. Of those columns, four were set in a desorption zone, three were in a concentration zone, three were in an adsorption zone, and two were in a desorbent recovery zone in a simulated-moving bed line. A mixture of chloroethylbenzene (CEB) isomers was applied to the simulated-moving bed line, and the adsorbing and separating capabilities of the adsorbent in the line were checked. The starting CEB isomer mixture applied had a composition of o-CEB/m-CEB/p-CEB=33/47/20. As the desorbent, used was xylene. The operation temperature was 130° C. The capabilities curve is shown in FIG. 4.

Comparative Example 1

An adsorbent was prepared in the same manner as in Example 1, except that the extruded grains were not rounded with a Marumerizer. The packing density of the adsorbent prepared herein was 0.49 g/ml. The pore volume of the adsorbent was measured, and the data are shown in FIG. 3. The adsorbent had a porosity of 0.38 cc/cc.

Using the adsorbent, the CEB isomer mixture was processed in the same manner as in Example 1 to check the adsorbing and separating capabilities of the adsorbent. The data obtained are shown in FIG. 4.

The data in FIG. 4 indicate that the most strongly adsorbable m-CEB was recovered in the extract flow and its purity in the flow was high. In addition, the data indicate that the adsorbent giving a higher ratio of m-CEB/ΣCEB (total of o-, m- and p-CEBs) in the extract flow and giving a lower ratio of m-CEB/ΣCEB in the raffinate flow has better adsorbing and separating capabilities. Obviously, it is seen that the adsorbent having an increased packing density of 0.54 mg/ml from 0.49 mg/ml and having a decreased porosity of 0.27 cc/cc from 0.38 cc/cc has better adsorbing and separating capabilities.

Example 2

An adsorbent paste was prepared in the same manner as in Example 1, except that Na-Y zeolite powder (from Toso) having a molar ratio $SiO_2/Al_2O_3$ of 5.5 was used herein, and this was extruded out through an extruder equipped with a 0.3 mm-mesh screen into adsorbent pellets.

In order to round them and to increase their packing density, the resulting pellets were processed in a rounding machine, Marumerizer, at a revolution of 850 rpm for 3 minutes.

Next, these were dried overnight at about 120° C. After having been dried, these were classified through a 80-mesh sieve to remove fine grains and through a 48-mesh sieve to remove coarse grains. The thus-classified grains were then calcined at 500° C. for 2 hours.

The calcined grains were treated in an aqueous solution containing 5% by weight of $KNO_3$, at a liquid/solid ratio (L/S) of 4 ml/g at about 80° C. for 1 hour. Next, these were washed with distilled water at a liquid/solid ratio of 4. The K ion exchanging treatment followed by washing with water was repeated 8 times. After this treatment, the grains were washed with distilled water at a liquid/solid ratio of 8, which was repeated 5 times.

Next, these grains were further subjected to ion exchanging treatment with an aqueous solution of 55 g of $PbNO_3$ dissolved in one liter of water, at room temperature for about 1 hour, and then washed with distilled water at a liquid/solid ratio of 4. The washing was repeated 5 times.

The thus-prepared adsorbent was dried overnight at about 120° C., and then calcined at 500° C. for 2 hours.

The diameter of the adsorbent grains was measured with a scale equipped with a magnifying glass, and it was 0.3 mm. The length of the grains varied from about 0.3 mm to about 0.6 mm. The packing density of the adsorbent was 0.65 g/ml. The pore diameter of the adsorbent grains was measured, and the data are shown in FIG. 3, which indicates the pore diameter distribution. The adsorbent had a porosity of 0.26 cc/cc.

The adsorbent was filled into 12 columns each having a size of 4.6 mmφ×1 m. Of those columns, four were set in a desorption zone, three were in a concentration zone, three were in an adsorption zone, and two were in a desorbent recovery zone in a simulated-moving bed line. A mixture of dichlorobenzene (hereinafter referred to as "DCB") isomers was applied to the simulated-moving bed line, and the adsorbing and separating capabilities of the adsorbent in the line were checked. The starting DCB isomer mixture applied had a composition of o-DCB/m-DCB/p-DCB=37/40/23. The desorbent, used was dichlorotoluene. The operation temperature was 130° C. The capabilities curve is shown in FIG. 5.

Example 3

An adsorbent was prepared in the same manner as in Example 2, except that the rounding treatment with a Marumerizer was effected at a revolution speed of 400 rpm for 1 minute. The packing density of the adsorbent was 0.60 g/ml. The pore volume of the adsorbent grains was measured, and the data are shown in FIG. 3. The adsorbent had a porosity of 0.35 cc/cc.

Figure 5:
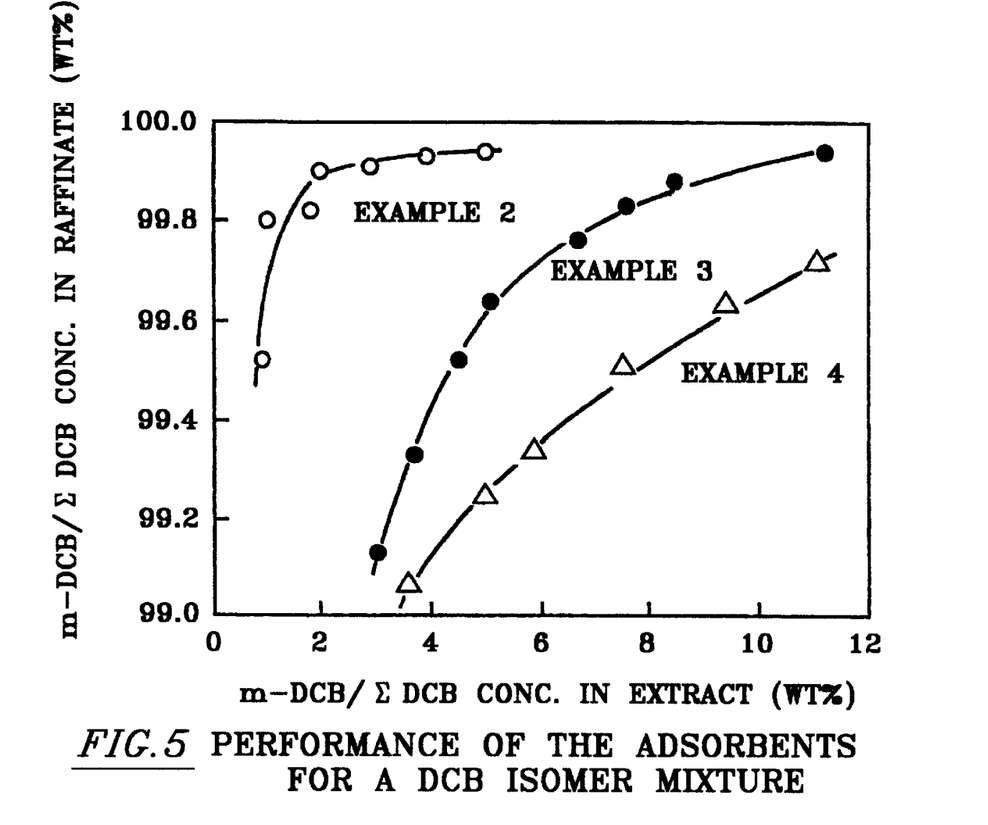
FIG. 5 is a graph showing the adsorbing and separating capabilities of the adsorbents for a DCB isomer mixture in Examples 2, 3 and 4.

The DCB adsorbing and separating capabilities of the adsorbent were checked in the same manner as in Example 2, and the data are shown in FIG. 5.

Example 4

An adsorbent was prepared in the same manner as in Example 2, except that the extruder was equipped with a 1.2 mm-mesh screen and that a 24-mesh sieve and a 10-mesh sieve were used for the grain classification.

The diameter of the adsorbent grains was measured with a scale equipped with a magnifying glass, and it was 1.2 mm. The length of the grains was 2.0 mm. The packing density of the adsorbent was 0.67 g/ml. The adsorbent had a porosity of 0.25 cc/cc.

The DCB adsorbing and separating capabilities of the adsorbent were checked in the same manner as in Example 2, and the data are shown in FIG. 5.

FIG. 5 indicates that the most weakly adsorbable m-DCB was recovered in the raffinate flow and its purity in the flow was high. In addition, the data in FIG. 5 indicate that the adsorbent giving a higher ratio of m-DCB/ΣDCB (total of o-, m- and p-DCBs) in the raffinate flow and giving a lower ratio of m-DCB/ΣDCB in the extract flow has better adsorbing and separating capabilities. Obviously, it is seen that the adsorbents in Examples 2 and 3 have better adsorbing and separating capabilities.

Example 5

An adsorbent for separating 2,4-dichlorotoluene (hereinafter referred to as DCT) was prepared according to the method of Example 3 in JP-A 5-70383. This adsorbing and separating agent is of X-type zeolite containing, as cations, sodium and strontium ions. This was calcined at 500° C. for 2 hours, and filled in a stainless steel column having an inner diameter of 4.6 mm and a length of 1 m. While m-xylene having been disoxidated through nitrogen bubbling (this m-xylene had a dissolved oxygen content of nearly 0 ppm, as measured with a polarographic dissolved oxygen meter) was introduced into the column at a constant flow rate, a small amount of a mixture of 2,4-, 2,5- and 2,6-DCTs and n-nonane that had been disoxidated in the same manner of nitrogen bubbling (this mixture had a dissolved oxygen content of nearly 0 ppm, as measured with a polarographic dissolved oxygen meter) was applied to the column for an instant, and the liquid flowing out through the outlet was sampled at predetermined intervals, and analyzed for its composition through gas chromatography. All the starting liquid used herein were previously dewatered through a molecular sieve. Time-dependently plotting the data of the analysis gives the concentration peak of each component. The selectivity of the adsorbing and separating agent could be represented by the ratio of the difference in the retention time (hereinafter referred to as "RT") between one isomer and n-nonane to that in the same between another isomer and n-nonane, as in the equation mentioned below. In general, adsorbents having a larger value for the selectivity to be obtained in that manner have better adsorbing and separating capabilities. N-nonane is substantially inactive to the adsorbing characteristic of zeolite.

Adsorptive Selectivity of Component A relative to Component B, $$\alpha(A/B) = \frac{(RT \text{ for Component } A) - (RT \text{ for n-nonane})}{(RT \text{ for Component } B) - (RT \text{ for n-nonane})}$$

The data obtained in this experiment are for the blank. The condition for the measurement is shown in Table 1.

TABLE 1

| Item | Condition | |
|---|---|---|
| Amount of Adsorbing and Separating Agent | about 10 g | |
| Flow Rate of m-xylene | 120 cc/hr | |
| Pulse Sample | n-C9 | 10 wt. % |
| | 2,4-DCT | 18 wt. % |
| | 2,5-DCT | 45 wt. % |
| | 2,6-DCT | 27 wt. % |
| | Amount | 10 µl |
| Temperature | 150° C. | |

Figure 6:
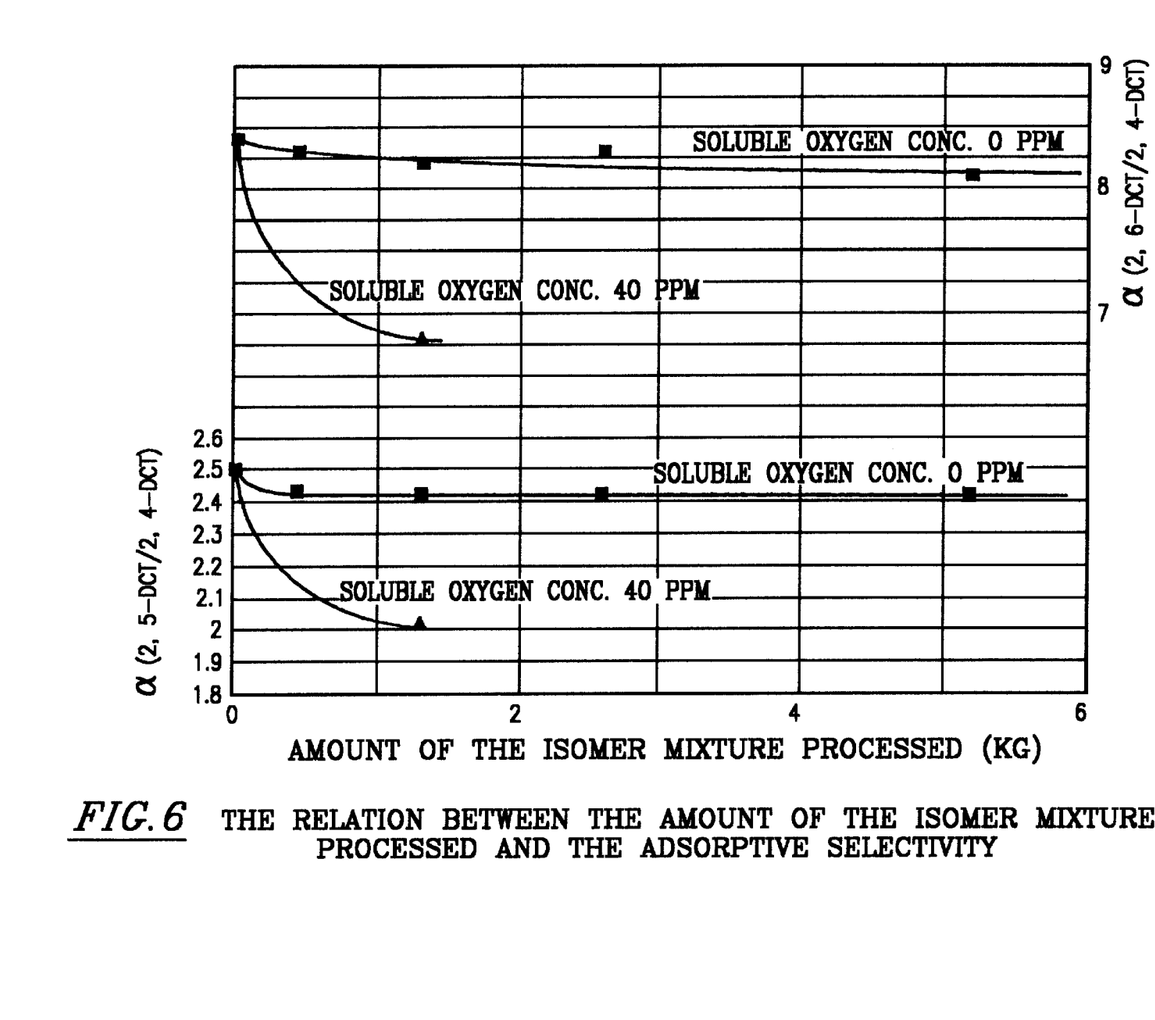
FIG. 6 is a graph showing the relationship between the amount of the isomer mixture processed and the adsorptive selectivity of the single isomer separated in Example 5 and Comparative Example 2.

Next, a mixture of m-xylene and dichlorotoluene that had been disoxidated through nitrogen bubbling and dewatered through a molecular sieve (this mixture had a dissolved oxygen content of nearly 0 ppm, as measured with a polarographic dissolved oxygen meter) was applied to the column. The amount of the mixture applied to the column was 520 times by weight the adsorbing and separating agent filled in the column. The liquid being flown out through the outlet of the column was sampled, and the adsorptive selectivity of the agent was determined in the same manner as above. The liquid flow condition in this experiment is shown in Table 2; and the flow rate-dependent adsorptive selectivity of the adsorbent tested herein is shown in FIG. 6.

TABLE 2

| Item | Condition | |
|---|---|---|
| WHSV (hr$^{-1}$) | 64 | |
| Mixture Composition | m-xylene | 80 wt. % |
| | 2,4-DCT | 4 wt. % |
| | 2,5-DCT | 10 wt. % |
| | 2,6-DCT | 6 wt. % |
| Temperature | 150° C. | |

Comparative Example 2

The adsorptive selectivity for the blank was determined in the same manner as in Example 5. The same experiment as in Example 5 was repeated except that a mixture of m-xylene and dichlorotoluene that had been dewatered through a molecular sieve but not disoxidated through nitrogen bubbling (this mixture had a dissolved oxygen content of nearly 40 ppm, as measured with a polarographic dissolved oxygen meter) was applied to the column, and the adsorption selectivity of the adsorbent was determined in the same manner as above. The flow rate-dependent adsorptive selectivity of the adsorbent tested herein is shown in FIG. 6.

What is claimed is:

1. A method for separating an isomer from mixed halogenated aromatic isomers, which comprises processing said isomer to provide a mixture having a dissolved oxygen content of at most 15 ppm by weight, contacting an adsorbent formed by kneading a zeolite powder with water; extruding the resultant paste into pellets; and rounding said pellets to form absorbent particles having
        a) porosity of from 0.20 cc/cc to 0.37 cc/cc;
        b) packing density of from 0.50 g/ml to 0.70 g/ml; and
        c) grain size of from 0.1 mm to 1.0 mm;
    with said mixture of halogenated aromatic compound isomers having to thereby separate at least one said halogenated aromatic isomer from said mixture.

2. The method for separating halogenated aromatic compounds as claimed in claim 1, wherein the halogenated aromatic compound isomer mixture is, prior to being contacted with said adsorbent, processed to remove dissolved oxygen therefrom, through a process selected from the group consisting of radiation, degassing, distillation and nitrogen sealing.

3. The method for separating halogenated aromatic compounds, as claimed in claim 1, wherein said halogenated aromatic compound contains in its formula at least one chlorine atom.

4. The method for separating halogenated aromatic compounds as claimed in claim 1, wherein said halogenated aromatic compound has in its formula at least one alkyl group.

5. A method for separating mixed halogenated aromatic isomers, comprising passing said mixed halogenated aromatic isomers into an adsorbent formed by kneading a zeolite powder with water; extruding the resultant paste into pellets; and rounding said pellets to form absorbent particles having
        a) porosity of from 0.20 cc/cc to 0.37 cc/cc;
        b) packing density of from 0.50 g/ml to 0.70 g/ml; and
        c) grain size of from 0.1 mm to 1.0 mm;
    to separate at least one said halogenated aromatic compound isomer from said mixture of said halogenated aromatic compound isomers.

6. The method for separating halogenated aromatic compounds, as claimed in claim 5, wherein said halogenated aromatic compound contains in its formula at least one chlorine atom.

7. The method for separating halogenated aromatic compounds as claimed in claim 5, wherein said halogenated aromatic compound has in its formula at least one alkyl group.

* * * * *